United States Patent
Molz, IV et al.

(10) Patent No.: US 7,625,394 B2
(45) Date of Patent: Dec. 1, 2009

(54) COUPLING ASSEMBLIES FOR SPINAL IMPLANTS

(75) Inventors: Fred J. Molz, IV, Collierville, TN (US); Jeff R. Justis, Collierville, TN (US)

(73) Assignee: Warsaw Orthopedic, Inc.

(*) Notice: Subject to any disclaimer, the term of this patent is extended or adjusted under 35 U.S.C. 154(b) by 500 days.

(21) Appl. No.: 11/197,799

(22) Filed: Aug. 5, 2005

(65) Prior Publication Data
US 2007/0043358 A1 Feb. 22, 2007

(51) Int. Cl.
*A61B 17/70* (2006.01)

(52) U.S. Cl. .............. 606/270; 623/17.11; 606/300; 606/279

(58) Field of Classification Search .......... 606/61, 606/72, 73, 246, 254, 255, 256, 257, 258, 606/259, 260, 261, 264, 266, 267, 268, 269, 606/270, 271, 272, 273, 274, 275, 276, 277, 606/278, 279, 300, 301, 302, 303, 305, 306, 606/307, 308, 309, 310; 623/17.11, 17.12, 623/17.13, 17.14, 17.15, 17.16; 403/324, 403/237, 373, 395, 400, 384, 398, 399
See application file for complete search history.

(56) References Cited

U.S. PATENT DOCUMENTS

| | | |
|---|---|---|
| 4,569,338 A | 2/1986 | Edwards |
| 4,827,918 A | 5/1989 | Olerud |
| 5,047,029 A | 9/1991 | Aebi et al. |
| 5,053,034 A | 10/1991 | Olerud |
| 5,176,680 A | 1/1993 | Vignaud et al. |
| 5,190,543 A | 3/1993 | Schlapfer |
| 5,234,431 A | 8/1993 | Keller |
| 5,254,118 A | 10/1993 | Mirkovic |
| 5,261,909 A | 11/1993 | Sutterlin et al. |
| 5,282,801 A | 2/1994 | Sherman |
| 5,527,314 A | 6/1996 | Brumfield et al. |
| 5,534,002 A | 7/1996 | Brumfield et al. |
| 5,545,166 A | 8/1996 | Howland |
| 5,562,662 A | 10/1996 | Brumfield |
| 5,569,247 A | 10/1996 | Morrison |
| 5,591,166 A | 1/1997 | Bernhardt et al. |
| 5,624,441 A | 4/1997 | Sherman et al. |
| 5,628,740 A | 5/1997 | Mullane |

(Continued)

FOREIGN PATENT DOCUMENTS

WO 98/27884 A1 7/1998

(Continued)

OTHER PUBLICATIONS

TiMX Comprehensive Low Back System, DePuy AcroMed, © 1999.

(Continued)

*Primary Examiner*—Eduardo C Robert
*Assistant Examiner*—Jan Christopher Merene (57) ABSTRACT

The forces exerted on a spinal implant by one or more coupling assemblies are controlled to facilitate the use of the implant in spinal stabilization and other procedures. The coupling assemblies are structured to distribute the forces exerted on the implant while engaging the implant to the coupling assembly and providing at least one of a rigid, semi-rigid or variable engagement of the coupling assembly with one or more anatomical structures of the spinal column.

35 Claims, 4 Drawing Sheets

U.S. PATENT DOCUMENTS

| | | | |
|---|---|---|---|
| 5,643,263 A | 7/1997 | Simonson | |
| 5,725,528 A | 3/1998 | Errico et al. | |
| 5,735,851 A | 4/1998 | Errico et al. | |
| 5,782,833 A | 7/1998 | Haider | |
| 5,800,435 A | 9/1998 | Errico et al. | |
| 5,885,285 A | 3/1999 | Simonson | |
| 5,904,683 A | 5/1999 | Pohndorf et al. | |
| 5,910,142 A | 6/1999 | Tatar | |
| 5,938,663 A | 8/1999 | Petreto | |
| 5,947,967 A | 9/1999 | Barker | |
| 6,010,503 A * | 1/2000 | Richelsoph et al. | 606/61 |
| 6,010,504 A | 1/2000 | Rogozinski | |
| 6,050,997 A | 4/2000 | Mullane | |
| 6,113,601 A | 9/2000 | Tatar | |
| 6,132,432 A | 10/2000 | Richelsoph | |
| 6,183,473 B1 | 2/2001 | Ashman | |
| 6,187,005 B1 | 2/2001 | Brace et al. | |
| 6,210,413 B1 | 4/2001 | Justis | |
| 6,248,107 B1 | 6/2001 | Foley | |
| 6,267,765 B1 | 7/2001 | Taylor et al. | |
| 6,296,642 B1 * | 10/2001 | Morrison et al. | 606/61 |
| 6,315,779 B1 | 11/2001 | Morrison et al. | |
| 6,352,537 B1 | 3/2002 | Strnad | |
| 6,355,038 B1 | 3/2002 | Pisharodi | |
| 6,478,798 B1 | 11/2002 | Howland | |
| 6,485,491 B1 | 11/2002 | Farris et al. | |
| 6,520,962 B1 | 2/2003 | Taylor et al. | |
| 6,524,315 B1 | 2/2003 | Selvitelli et al. | |
| 6,547,790 B2 | 4/2003 | Harkey, III et al. | |
| 6,562,038 B1 | 5/2003 | Morrison | |
| 6,565,565 B1 * | 5/2003 | Yuan et al. | 606/61 |
| 6,626,906 B1 | 9/2003 | Young | |
| 6,685,705 B1 | 2/2004 | Taylor et al. | |
| 6,770,075 B2 | 8/2004 | Howland | |
| 6,783,527 B2 | 8/2004 | Drewry et al. | |
| 6,835,196 B2 * | 12/2004 | Biedermann et al. | 606/61 |
| 7,066,937 B2 * | 6/2006 | Shluzas | 606/86 A |
| 7,081,116 B1 | 7/2006 | Carly | |
| 7,087,057 B2 * | 8/2006 | Konieczynski et al. | 606/73 |
| 2002/0133159 A1 | 9/2002 | Jackson | |
| 2003/0100896 A1 * | 5/2003 | Biedermann et al. | 606/61 |
| 2003/0100904 A1 * | 5/2003 | Biedermann | 606/73 |
| 2003/0149431 A1 * | 8/2003 | Varieur | 606/61 |
| 2003/0153911 A1 * | 8/2003 | Shluzas | 606/61 |
| 2004/0260283 A1 | 12/2004 | Wu et al. | |
| 2005/0131410 A1 | 6/2005 | Lin | |
| 2005/0240180 A1 | 10/2005 | Vienney et al. | |
| 2006/0241595 A1 | 10/2006 | Molz, IV et al. | |
| 2007/0055244 A1 * | 3/2007 | Jackson | 606/61 |
| 2007/0161999 A1 * | 7/2007 | Biedermann et al. | 606/61 |
| 2007/0167949 A1 * | 7/2007 | Altarac et al. | 606/61 |
| 2008/0154315 A1 * | 6/2008 | Jackson | 606/309 |
| 2008/0215100 A1 * | 9/2008 | Matthis et al. | 606/309 |

FOREIGN PATENT DOCUMENTS

| | | | |
|---|---|---|---|
| WO | 00/76413 A1 | 12/2000 | |
| WO | 01/15612 A1 | 3/2001 | |
| WO | 03/024343 | 3/2003 | |
| WO | WO/03/024343 * | 3/2003 | 606/270 |
| WO | WO 2006/115954 | 11/2006 | |

OTHER PUBLICATIONS

Pass® Deformity System, Encore Surgical, © Jan. 2002.
Spine Internal Fixation Device, Encore Surgical, © Jan. 2002.

* cited by examiner

Fig. 5 ments or parts to secure the implant to the screw that make

COUPLING ASSEMBLIES FOR SPINAL IMPLANTS

BACKGROUND

Spinal implants can be engaged to or along one or more vertebrae of the spinal column for the treatment of various spinal conditions. Fasteners can be provided to secure the implant to a particular location along the spinal column. The implants can be provide to stabilize the spinal column for treatment, either by fixing the spinal column or by permitting at least some motion of the stabilized motion segments.

Coupling assemblies such as multi-axial and uni-axial screws have been employed for securing elongated implants, such as rods or plates, along one or more motion segments of the spinal column. Such screws can comprise many components or parts to secure the implant to the screw that make placement and manipulation during surgery cumbersome. Furthermore, coupling assemblies can be configured so that limited surface area contact is provided between implant and the coupling assembly, resulting in a less than optimal securement arrangement therebetween.

SUMMARY

According to one aspect, a system for stabilizing a bony segment comprises an implant and a coupling assembly engageable to the implant. The coupling assembly comprises an anchor member engageable to the bony segment and a receiver member extending from the anchor member that defines a passage for receiving the implant. The passage has a length between opposite end openings of the receiver member and the implant extends along the length through the end openings. The coupling assembly further includes a seat member positioned between the implant and the anchor member that includes a concave implant support surface. The coupling assembly also includes a securing member with a concave implant engaging surface. The securing member is threadingly engageable to a securing position in the receiver member while the implant engaging surface is maintained in aligned relation with the implant support surface. In the securing position, the implant is engaged along the length by the implant support surface and the implant engaging surface.

According to another aspect, a system for stabilizing a bony segment comprises an implant and a coupling assembly engageable to the implant. The coupling assembly comprises an anchor member engageable to the bony segment, a receiver member coupled to the anchor member that defines a passage for receiving the implant; a seat member positioned between the implant and the anchor member, and a securing member. The seat member includes an implant support surface oriented toward the implant and the securing member includes an implant engaging surface. The securing member and implant engaging surface are axially moveable in the receiver member to position the implant in contact with the implant engaging surface and the implant support surface. The securing member engages the seat member to rotationally constrain the implant engaging surface relative to the implant support surface as the securing member is axially moved in the receiver member to engage the implant between the implant support surface and the implant engaging surface.

According to another aspect a system for stabilizing a bony segment comprises an implant and a coupling assembly engageable to the implant. The coupling assembly includes an anchor member engageable to the bony segment; a receiver member coupled to the anchor member that defines a passage for receiving the implant; a seat member positioned between the implant and the anchor member, and a securing member. The seat member includes an implant support surface oriented toward the implant and the securing member includes an implant engaging surface. One of the securing member and the seat member includes at least one axially extending side channel and the other of the securing member and the seat member includes at least one axially extending finger received in the at least one side channel as the securing member and the implant engaging surface are axially moved in the receiver member to engage the implant between the implant engaging surface and the implant support surface.

According to another aspect, a method for securing an implant to the spinal column comprises: engaging an anchor member to a vertebra; positioning an implant in a receiver member extending from the anchor member; engaging a securing member to the receiver member; threadingly advancing the securing member into the receiver member to contact the implant with an implant engaging surface of the securing member; rotationally constraining the implant engaging surface as the securing member is threadingly advanced in the receiver member; and engaging the implant between the implant engaging surface and an implant support surface in the receiver member.

According to another aspect, a method for securing a spinal rod to an anchor member includes providing a coupling assembly sized for engagement with a vertebra. The coupling assembly includes an anchor member engageable to the vertebra, a receiver member extending from said anchor member and defining a passage for receiving said rod, the receiver member further including an implant support surface along the passage, and a securing member including an implant engaging surface. The method further includes configuring the coupling assembly for engaging the spinal rod in the passage between the implant support surface and the implant engaging surface and limiting engagement stresses exerted on the rod by providing each of the implant engaging surface and the implant support surface in a configuration that conformingly contacts the rod to distribute engagement forces.

These and other aspects will be discussed further below.

DETAILED DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Coupling assemblies are provided to secure one or more implants along the spinal column while providing a distributed exertion of forces by the coupling assembly on the implant. The coupling assemblies each include an anchor member for engaging the coupling assembly to an underlying bony structure, a receiver member for receiving the implant, and a securing member for securing the implant to the receiver member. The coupling assemblies also include a seat member in the receiver member, and the implant is secured between the seat member and the securing member. The seat member and securing member are structured to distribute the securing forces along and about the implant and align the engaging surfaces with one another to reduce or minimize concentration of stresses on the implant, which could result in an undesirable alteration of the implant or provide less than optimal securing arrangements with the coupling assembly.

Referring to FIGS. 1-3B, there is shown a coupling assembly 10 including an anchor member 12, a receiver member 20 coupled to anchor member 12, and a securing member 40. Anchor member 12 and receiver member 20 include a non-pivoted orientation shown in FIGS. 3A and 3B where each extends along a longitudinal axis 11. Anchor member 12 can be pivotal relative to receiver member 20 to any one of an infinite number of positions defining a cone about axis 11. Non-pivotal and fixed arrangements between anchor member 12 and receiver member 20 are also contemplated.

An implant 60 is positionable on, in or about receiver member 20, and securing member 40 is movable relative to implant 60 and receiver member 20 to secure implant 60 to coupling assembly 10. Coupling assembly 10 includes a seat member 30 between anchor member 12 and implant 60 that includes an implant support surface for contacting and supporting implant 60. The implant can be engaged along one or more vertebrae of the spinal column with one or more coupling assemblies 10 or any other type of fastener in combination with one or more coupling assemblies 10 to provide, for example, a spinal stabilization system.

Receiver member 20 includes a lower portion 22 in the form of a bowl that is configured to form a receptacle to receive a head 18 of anchor member 12 therein. Head 18 of anchor member 12 is pivotally captured and retained in receiver member 20 with a retaining clip 19. Other means for securing anchor member 12 in receiver member 20 are also contemplated, including forming the lower opening of receiver member 20 to retain head 18, providing retaining structures such as collars, washers, bushings, or other devices.

A pair of arms 24 extend axially from opposite sides of lower portion 22 to form a saddle arrangement to receive implant 60 and engage securing member 50. Receiver member 20 further includes seat member 30 positioned between arms 24 adjacent head 18 of anchor member 12. In one embodiment, seat member 30 includes a distally oriented socket 32 that pivotally receives head 18. Opposing arms 24 define an implant receiving portion 21 therebetween that is sized to receive implant 60 proximally of seat member 30. Arms 24 can each include an internal thread profile to threadingly engage securing member 40, although other engagement structures to engage securing member 40 and receiver member 20 to one another are contemplated. Arms 24 also each include a hole 28 to receive and facilitate engagement by and manipulation with insertion and/or reduction instrumentation (not shown.)

Securing member 40 is movably engageable with receiver member 20 to secure implant 60 in engagement with seat member 30. Securing member 40 can include a proximal break-off portion 42 and a receiver engaging portion 44, although embodiments without break-off portion 42 are contemplated. Receiver engaging portion 44 is illustrated as an externally threaded set screw that engages the internal thread profile along arms 24, although other configurations are contemplated.

A proximally opening first tool recess 46 is formed in break-off portion 42, and a proximally opening second tool recess 48 is formed in receiver engaging portion 44 adjacent to and in communication with first tool recess 46. A driving tool in first tool recess 46 can be manipulated to move securing member 40 relative to receiver member 20 and into engagement with implant 60 until sufficient resistance to movement of securing member 40 is encountered to create torque to remove break-off portion 42. Second tool recess 48 is accessible to allow a tool to be positioned therein to apply force to tighten or loosen securing member 40 even when break-off portion 42 is removed.

Securing member 40 further comprises a distal implant engaging portion 50 that is mounted to and rotatable relative to engaging portion 44. In the illustrated embodiment, implant engaging portion 50 includes a coupling arm 55 extending proximally therefrom. Coupling arm 55 is received and axially constrained in central opening 45 of receiver engaging portion 44. In the illustrated embodiment, as shown in further detail in FIGS. 3B and 5, coupling arm 55 includes a number of axially extending tabs with enlarged ends forming radially outwardly extending lips that contact a surface extending about central opening 45 to axially restrain and rotatably capture implant engaging portion 50 on receiver engaging portion 44. Accordingly, as receiver engaging portion 44 is threadingly engaged along arms 24, distal implant engaging portion 50 can advance linearly toward implant 60.

Implant engaging portion 50 includes opposite distal extensions 51 each defining a distally oriented end surface 52. Extensions 51 extend along opposite sides of implant 60 when implant engaging surface 54 is positioned against implant 60. Extensions 51 rotationally constrain implant engaging portion 50 by contacting implant 60 as receiver engaging portion 44 is engaged to and moved axially along receiver member 20. An implant engaging surface 54 extends between distal extensions 51, forming a distally oriented U-shaped surface that is positioned substantially entirely in contact with the proximally directed portion of the outer surface of implant 60. In the illustrated embodiment, implant engaging surface 54 is concavely curved, although non-curved shapes are also contemplated.

Seat member 30 includes a central opening 37 that is in communication with head 18 of anchor member 12 to receive a driving tool (not shown) to apply a driving force to anchor member 12. Seat member 30 includes a proximally oriented implant support surface 34 defining a lower or distal portion of implant receiving portion 21. Implant support surface 34 extends between proximal extensions 36, forming a proximally oriented U-shaped surface that is positioned substantially entirely in contact with the distally oriented portion of the outer surface of implant 60. In the illustrated embodiment, implant support surface 34 is concavely curved, although non-curved shapes are also contemplated. Implant support surface 34 is defined at least in part by proximal extensions 36 of seat member 30.

Proximal extensions 36 each include a proximally oriented end surface 38. Surfaces 38, 52 are aligned with one another when coupling assembly 10 is assembled and implant 60 is positioned between surfaces 34, 54. When implant engaging surface 54 and implant support surface 34 are positioned in contact with implant 60, proximal end surfaces 38 are spaced from the respective adjacent distal end surfaces 52 of securing member 40. This permits the full securing force applied to securing member 40 to be distributed to implant 60 between support surface 34 and engaging surface 54.

Implant support surface 34 and implant engaging surface 54 are moveable toward one another to an implant securing position where surfaces 34, 54 are positioned firmly in contact with implant 60. Extensions 36, 51 extend along the sides of implant 60, which in turn allows seat member 30 and implant engaging portion to self-align with implant 60 positioned therebetween. Surfaces 34, 54 are sized and shaped to extend about the respective proximally and distally directed outer surface portions of implant 60 so that the contact surface area is maximized. In one embodiment, implant 60 defines a length L along implant receiving portion 21 and between the locations where implant 60 enters and exits the space between arms 24. Surfaces 34, 54 extend along substantially the entirety of this length L of implant 60 to maximize surface area contact with implant 60.

In use, anchor member 12 is engaged to an underlying bony structure with receiver member 20 positioned to receive implant 60. Implant 60 is positioned in implant receiving portion 21 of receiver member 20 along or adjacent implant support surface 34 of seat member 30. In the illustrated embodiment, implant receiving portion 21 forms a passage extending along length L between the opposite end openings of arms 24 of receive member 20. Securing member 40 is engaged to receiver member 20, and advanced therealong until implant engaging surface 54 contacts implant 60. In this configuration, distal end surfaces 52 of implant engaging portion 50 are spaced from the respective aligned proximal end surfaces 38 of seat member 30. As securing member 40 is further advanced distally in receiver member 20, implant engaging portion 50 is maintained in contact with implant 60 while receiver engaging portion 44 is threadingly engaged with receiver member 20 until sufficient resistance is encountered to sever break-off portion 42.

Figure 1:
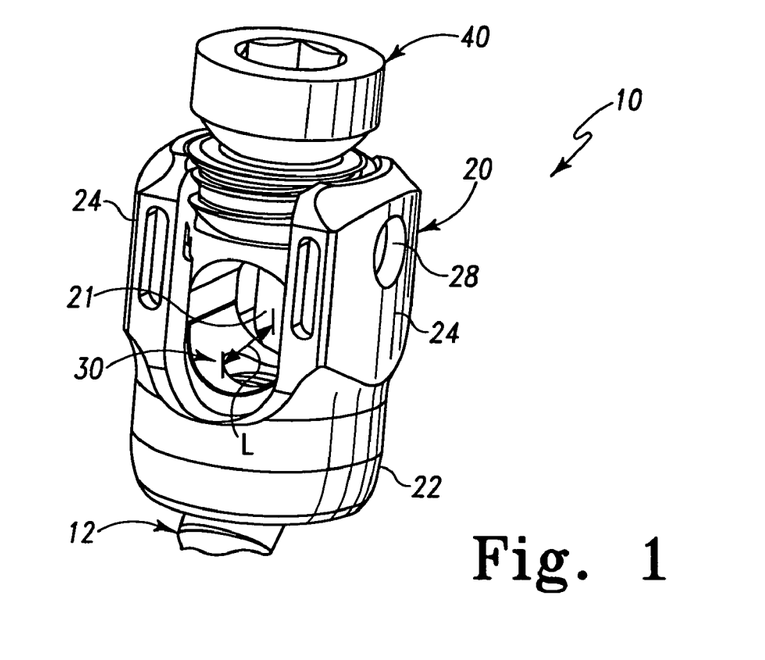
FIG. 1 is a perspective view of one embodiment coupling assembly.
Figure 2:
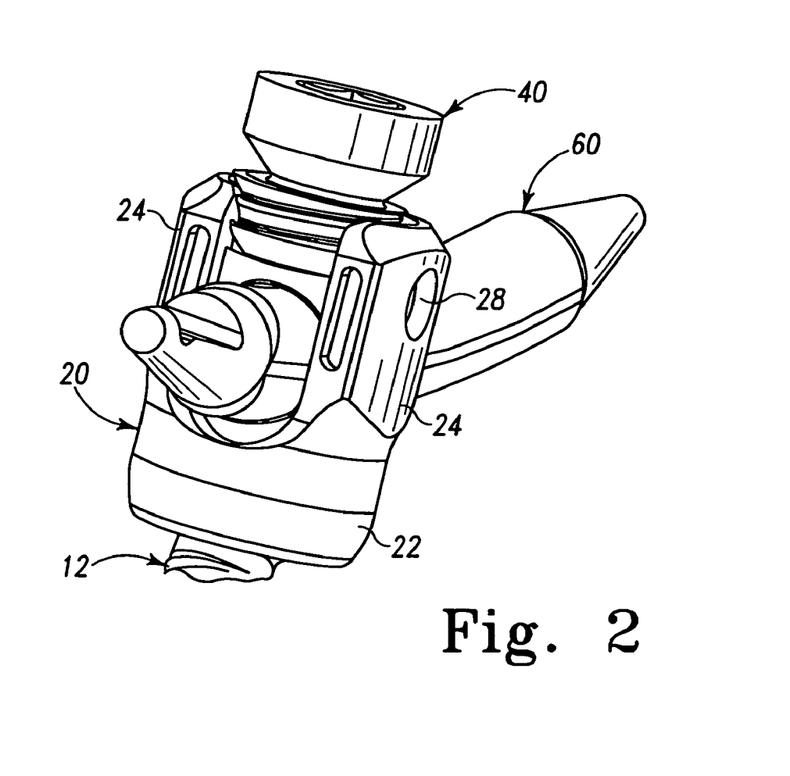
FIG. 2 is the coupling assembly of FIG. 1 with an implant positioned for engagement with the coupling assembly.
Figure 3A:
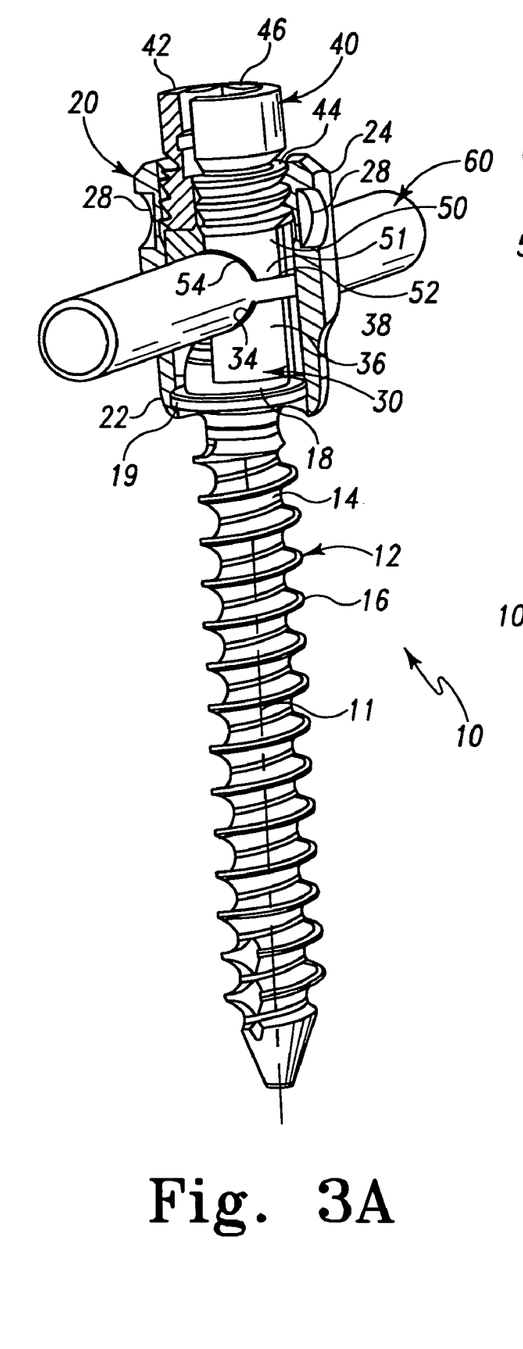
FIGS. 3A and 3B are partial sectional views of the coupling assembly of FIG. 1 with an implant extending therethrough.
Figure 3B:
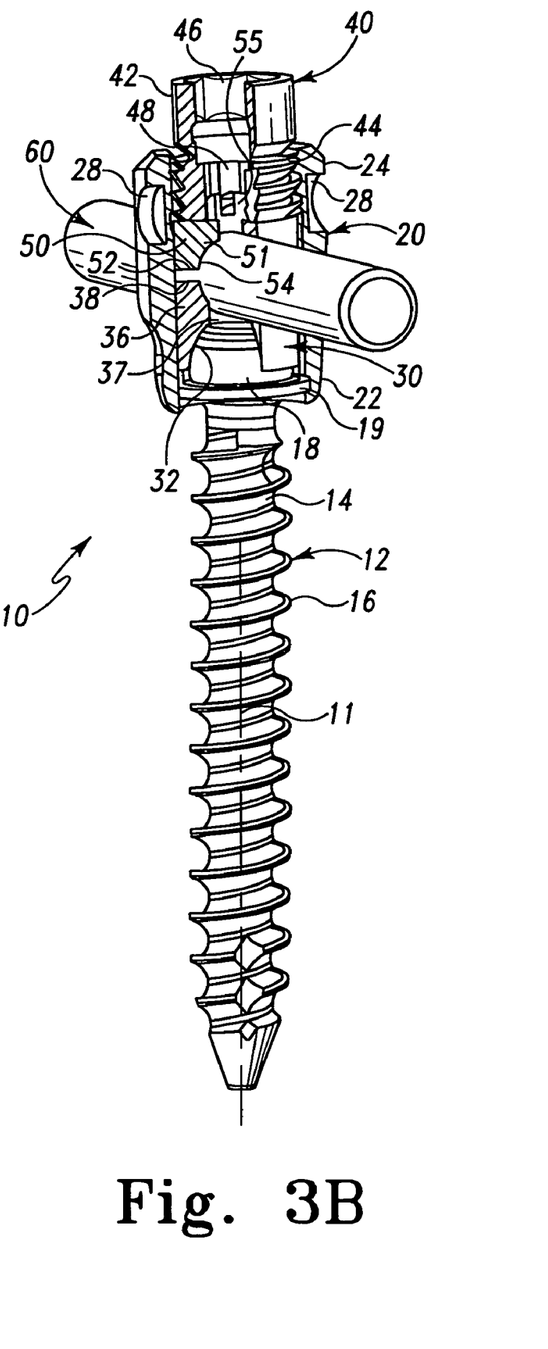

As securing member 40 is further advanced distally in receiver member 20, it simultaneously moves seat member 30 distally. In one embodiment, this positions seat member 30 into contact with head 18 of anchor member 12 to rigidly fix anchor member 12 in receiver member 20. Other embodiments contemplate that anchor member 12 maintains a variable angle or semi-rigid arrangement relative to receiver member 20 even when securing member 40 and seat member 30 are firmly engaged to implant 60.

The surface areas of support surface 34 and engaging surface 54 in contact with implant 60 provide a desired frictional or clamping engagement with implant 60 to maintain implant 60 in position relative to coupling assembly 10, but distribute the forces applied to preserve, maintain or prevent substantial alteration of one or more desired characteristics of implant 60. For example, implant 60 can be made from a polymer material, and the force distribution prevents securing member 40 and or seat member 30 from piercing, punching, cutting, compressing, or otherwise deforming implant 60 in an undesired fashion. The characteristics of implant 60 for which alteration can be prevented or limited can include any one or combination of surface profile, cross-sectional size, cross-sectional shape, cross-sectional area, compression stress, and shear stress, for example.

Anchor member 12 in the illustrated embodiment is a bone screw and includes a shaft 14 having a thread profile 16 therealong and enlarged head 18 at a proximal end of anchor member 12. Head 18 includes a tool recess (not shown) to receive a driving tool to facilitate engagement of anchor member 12 to the underlying bone and ridges along an upper surface thereof that are engaged by seat member 30 to lock the anchor members 12 in position relative to receiver member 20. Various forms for anchor member 12 are contemplated, including threaded and non-threaded anchors, uni-axial and multi-axial arrangements, hooks, clamps, spikes, cables, interbody implants, fusion devices, non-cannulated screws, fenestrated screws, and bolts, for example.

Figure 4:
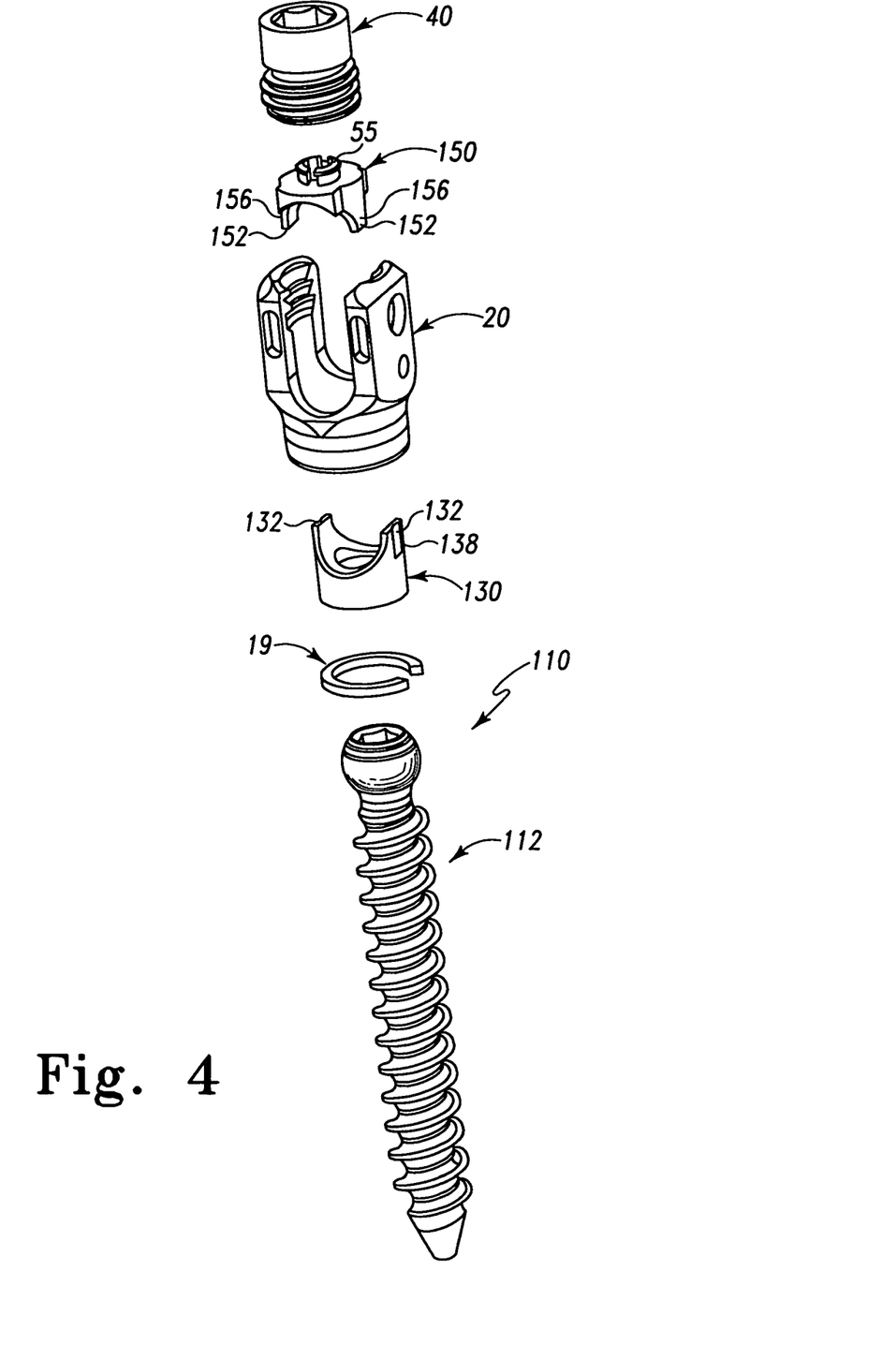
FIG. 4 is an exploded view of another embodiment coupling assembly.
Figure 5:
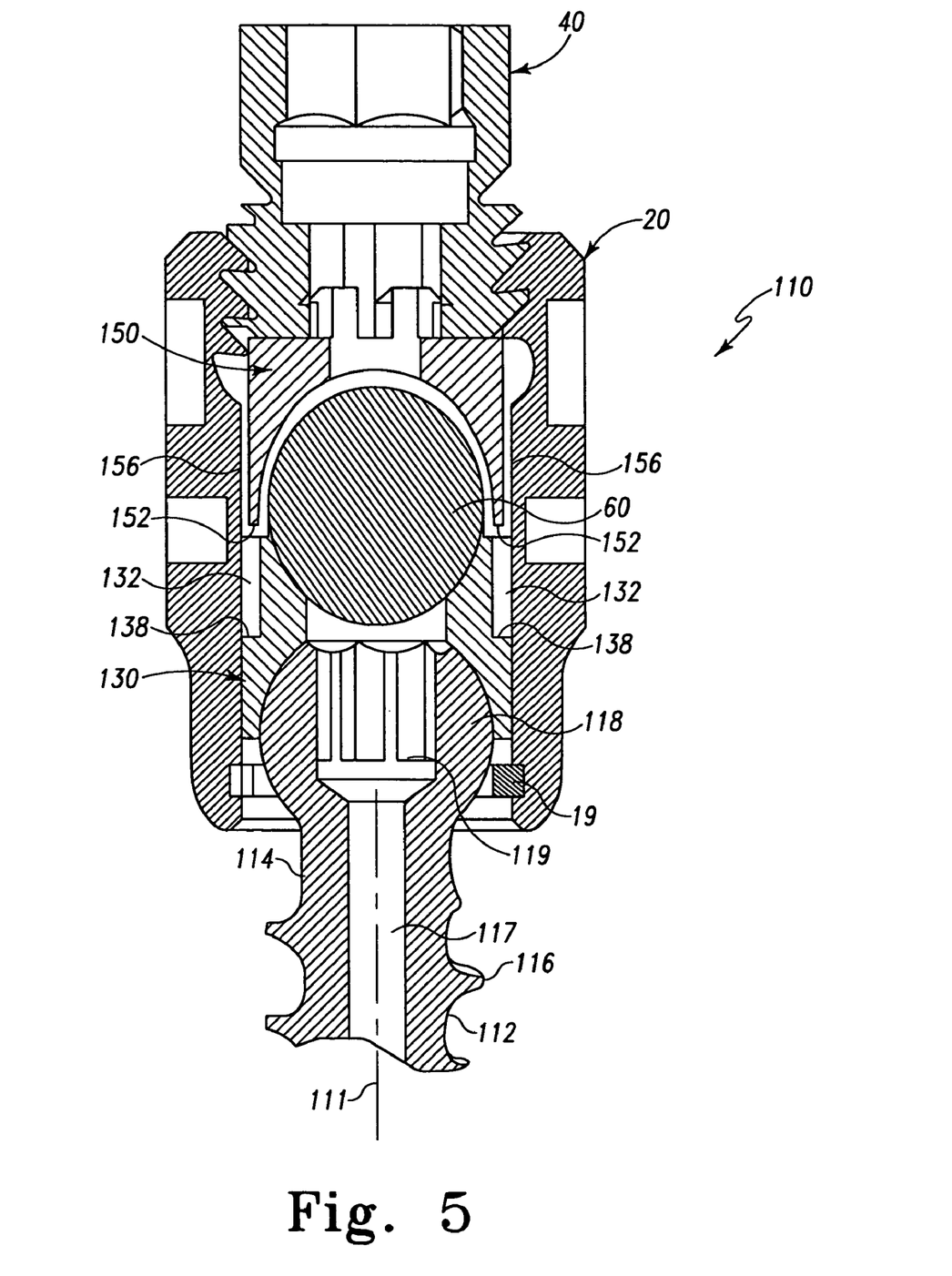
FIG. 5 is another section view of the coupling assembly of FIG. 4 with an implant extending therethrough.

Another embodiment coupling assembly 110 is shown in FIGS. 4 and 5. Coupling assembly 110 is similar to coupling assembly 10, and identical components are indicated with the same reference numerals provided above for coupling assembly 10. In one form, coupling assembly 110 includes a seat member and an implant engaging portion that are rotationally constrained relative to one another and axially moveable relative toward one another until the implant is engaged therebetween.

Coupling assembly 110 includes an anchor member 112 in the form of a screw having a shaft 114 extending along a longitudinal axis 111. Shaft 114 includes thread profile 116 and an enlarged head 118 at the proximal end of shaft 114. Shaft 114 includes a cannulation 117 extending along axis 111. Cannulation 117 opens into proximal tool recess 119 and also at the distal end of shaft 114. Cannulation 114 can facilitate placement of anchor member 112 over a guide wire or other guiding device, and to provide an avenue for delivery of bone cement or other therapeutic substances into the bone. Other embodiments contemplate that anchor member 112 does not include a cannulation 117. Still other embodiments contemplate any suitable form for the anchor member as discussed above with respect to anchor member 12.

Coupling assembly 110 includes a seat member 130 similar to seat member 30, but includes outwardly opening side channels 132 extending axially therealong on opposites sides thereof. Side channels 132 include proximally oriented surfaces 138 at the lower ends thereof. Securing member 40 includes another embodiment implant engaging portion 150 that is similar to implant engaging portion 50, but includes distally extending fingers 156 that are sized and spaced to be received in respective ones of the side channels 132 of seat member 130 with implant 60 between seat member 130 and implant engaging portion 150.

Distal end surfaces 152 of fingers 156 are spaced from the proximally oriented surfaces 138 of channels 132 to allow axial movement of seat member 130 and implant engaging portion 150 relative to one another. Receipt of fingers 156 in channels 132 rotationally constrains implant engaging portion 150 and seat member 130 relative to one another. The implant supporting surface 134 and implant engaging surface 154 are thus maintained in alignment with one another, facilitating placement of each of these surfaces in contact with the outer surfaces of implant 60 in an aligned manner.

In another embodiment, implant engaging portion 150 includes side channels, and seat member 130 includes proximally extending fingers positionable in the side channels. In another embodiment, only one finger/channel interface is provided. In yet another embodiment, more than two finger/channel interfaces are provided.

Implant 60 can be structured either alone or in combination with one or more other implants and/or coupling assemblies to provide a desired stabilization effect. Implant 60 includes a characteristic for which it is desirable to control or limit the coupling forces exerted by coupling assembly 10, 110 on implant 60. For example, implant 60 can be made from a material that can be damaged, deformed, or otherwise undesirably altered when securing member 40 is engaged with receiver member 20 in a manner that sufficiently secures implant 60 in receiver member 20.

In the illustrated embodiment, implant 60 is an elongated spinal rod structured to extend between at least two coupling assemblies 10, 110 to stabilize a motion segment between the at least two coupling assemblies. Various forms for implant 60 are contemplated, including rods, tethers, cables, wires, plates, and staples, for example. In one specific embodiment, implant 60 is a spinal rod comprised of any one or combination of plastic, polymer, tissue, fabric, or mesh material. Other embodiments contemplate that implant 60 can be made from any suitable biocompatible material. Implant 60 can have a length adapted to extend along multiple vertebral levels.

In spinal surgical procedures, implant 60 and the coupling assemblies 10, 110 discussed herein may be employed unilaterally. Alternatively, a second implant 60 and coupling assemblies 10, 110 can be secured to the other side of the vertebral level or levels to be stabilized. Multiple implants 60 and corresponding coupling assemblies 10, 110 can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The coupling assemblies and implants can be positioned along the spinal column in invasive procedures where skin and tissue are dissected and retracted to expose the implant locations, or in minimally invasive procedures where one or more the anchor assemblies and implants are guided through at least the tissue or access portals adjacent the column to the desired implantation location.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for stabilizing a bony segment, comprising: an implant;
   a coupling assembly engageable to said implant, wherein said coupling assembly comprises:
   an anchor member engageable to the bony segment, wherein the anchor member extends along a longitudinal axis between a proximal end and a distal end;
   a receiver member extending from said proximal end of said anchor member and defining a passage for receiving said implant, said passage having a length between opposite end openings of said receiver member, said implant extending transversely to said longitudinal axis along said length and through said end openings;
   a seat member positioned between said implant and said anchor member, said seat member including an implant support surface extending at least partially about said implant, wherein said seat member is movable distally in said receiver member to contact said proximal end of said anchor member and said seat member includes at least one outwardly opening side channel in a side thereof that opens proximally; and
   a securing member including an implant engaging surface extending at least partially about said implant and at least one finger extending distally from said implant engaging surface into said at least one side channel of said seat member so that a portion said seat member is positioned between a distal end of said at least one finger and said implant, said securing member being engageable to a securing position in said receiver member while said implant engaging surface is maintained in aligned relation with said implant support surface with said at least one finger in said at least one side channel, wherein in said securing position said implant is engaged along said length by said implant support surface and said implant engaging surface.

2. The system of claim 1, wherein:
   said anchor member includes a screw having a head pivotally captured in said receiver member; and
   said seat member is positioned adjacent said head between said implant and said anchor member, said seat member including said implant support surface.

3. The system of claim 1, wherein the implant is an elongate spinal rod and said receiver member includes a lower portion for pivotally receiving said anchor member and a pair of arms extending from said lower portion, said arms defining said passage for receiving the implant therethrough.

4. The system of claim 1, wherein said securing member includes a receiver engaging portion threadingly engageable with said receiver member and a distal implant engaging portion coupled to said receiver engaging portion and rotatable relative thereto, said implant engaging surface being formed on a distally oriented face of said implant engaging portion.

5. The system of claim 4, wherein:
   said arms are internally threaded; and
   said receiver engaging portion includes an externally threaded body engageable to said arms.

6. The system of claim 5, wherein said securing member further includes an upper break-off portion extending proximally from said body, said break-off portion being severable from said body upon application of a threshold torque to said break-off portion.

7. The system of claim 4, wherein said receiver engaging portion includes a central opening extending therethrough and said implant engaging portion includes a coupling arm extending into said central opening and engaging said implant engaging portion in axial securement with said receiver engaging portion while permitting said implant engaging portion to rotate relative to said receiver engaging portion.

8. The system of claim 1, wherein said seat member includes:
   a body defining a distally opening socket configured to pivotally receive said anchor member;
   said implant support surface extending along said body on a proximal side of said body; and
   opposite extensions extending along opposite sides of said implant when said implant is positioned in contact with said implant support surface.

9. The system of claim 8, wherein said seat member includes a passage extending between said implant support surface and said socket.

10. The system of claim 9, wherein:
   said anchor member includes a screw with an enlarged head received in a distal portion of said receiver member and a shaft extending distally from said head through a distally oriented opening of said receiver member; and
   said coupling assembly includes a clip engaged to said receiver member and positioned about said shaft adjacent a distal side of said head, said clip pivotally capturing said screw in said receiver member.

11. The system of claim 1, wherein:
said implant engaging surface is defined along a distal face of an implant engaging portion of said securing member; and
with said implant positioned between said seat member and said implant engaging surface and with said securing member engaging to said receiver member, said implant engaging portion is rotationally constrained relative to said seat member and axially moveable towards and away from said implant.

12. The system of claim 11, wherein said seat member includes axially extending side channels that open outwardly in opposite directions from one another, and said implant engaging portion includes distally extending fingers on opposite sides thereof positioned in respective ones of said side channels.

13. The system of claim 12, wherein said side channels each include a proximally oriented end surface and said fingers each include a distally oriented end surface, said distally oriented end surfaces being spaced axially from a respective one of said proximally oriented end surfaces when said implant support surface and said implant engaging surface are in contact with said implant.

14. The system of claim 1, wherein said securing member threadingly engages to said receiver member.

15. The system of claim 1, wherein said implant support surface and said implant engaging surface are each concave.

16. A system for stabilizing a bony segment, comprising:
an implant;
a coupling assembly engageable to said implant, wherein said coupling assembly comprises:
an anchor member engageable to the bony segment extending along a longitudinal axis between a proximal end and a distal end;
a receiver member coupled to said anchor member at said proximal end and defining a passage for receiving said implant;
a seat member positioned in said receiver member between said implant and said anchor member, said seat member including an implant support surface oriented toward said implant; and
a securing member including an implant engaging surface, said securing member and said implant engaging surface being axially moveable in said receiver member to position said implant in contact with said implant engaging surface and said implant support surface, wherein at least one of said securing member and said seat member extends along said longitudinal axis toward the other of said securing member and said seat member in overlapping engagement therewith to rotationally constrain said implant engaging surface relative to said implant support surface as said securing member is axially moved in said receiver member to engage said implant between said implant support surface and said implant engaging surface, wherein said seat member includes axially extending side channels that open outwardly from said seat member in opposite directions from one another, and said securing member includes a distal implant engaging portion defining said implant engaging surface, said implant engaging portion including distally extending fingers on opposite sides thereof with distal ends positioned in respective ones of said side channels with a portion of said seat member positioned between said implant and said distal ends of said fingers in said side channels.

17. The system of claim 16, wherein:
said passage includes a length between opposite end openings of said receiver member, said implant extending along said length and through said end openings when positioned in said receiver member; and
said implant support surface and said implant engaging surface are concave and extend along said length with said implant positioned in said receiver member.

18. The system of claim 16, wherein said implant engaging surface and said implant support surface each include a concave curvature positionable about a respective portion of said implant when in contact therewith.

19. The system of claim 16, wherein said side channels each include a proximally oriented end surface and said fingers each include a distally oriented end surface, said distally oriented end surfaces being spaced axially from a respective one of said proximally oriented end surfaces when said implant is engaged between said implant engaging portion and said seat member.

20. The system of claim 16, wherein the implant is an elongate spinal rod and said receiver member includes a lower portion for receiving said anchor member and pair of arms extending from said lower portion, said arms defining said passage for receiving the implant therethrough.

21. The system of claim 20, wherein said securing member includes a receiver engaging portion threadingly engageable with said receiver member and a distal implant engaging portion coupled to said receiver engaging portion and rotatable relative thereto, said implant engaging surface being formed on a distally oriented face of said implant engaging portion.

22. The system of claim 21, wherein:
said arms are internally threaded; and
said receiver engaging portion includes an externally threaded body engageable to said arms.

23. The system of claim 16, wherein said seat member includes:
a body defining a distally opening socket configured to pivotally receive said anchor member;
said implant support surface extending along said body on a proximal side of said body; and
opposite extensions extending along opposite sides of said implant when said implant is positioned in contact with said implant support surface.

24. A system for stabilizing a bony segment, comprising:
an implant;
a coupling assembly engageable to said implant, wherein said coupling assembly comprises:
an anchor member engageable to the bony segment;
a receiver member coupled to said anchor member and defining a passage for receiving said implant;
a seat member positioned in said receiver member between said implant and said anchor member, said seat member including an implant support surface oriented toward and contacting said implant; and
a securing member including an implant engaging portion defining a distally facing implant engaging surface, wherein one of said implant engaging portion and said seat member includes at least one axially extending side channel and the other of said implant engaging portion and said seat member includes at least one axially extending finger received in said at least one side channel as said securing member and said implant engaging portion are axially moved in said receiver member to engage said implant between said implant engaging surface and said implant support surface, wherein a portion of said seat member is positioned between said implant and a distal end of said at least one axially extending finger that is received in said at least one side channel.

25. The system of claim 24, wherein said at least one finger and said at least one channel engage one another to rotationally constrain said implant engaging surface relative to said implant support surface as said securing member is threadingly engaging in said receiver member.

26. The system of claim 25, wherein said at least one side channel includes a proximally oriented end surface and said at least one finger includes a distally oriented end surface, said distally oriented end surface being spaced axially from said proximally oriented end surface when said implant is engaged between said implant engaging portion and said seal member.

27. The system of claim 26, wherein said at least one side channel includes a pair of side channels that open outwardly of said seat member on opposite sides of said seat member and said at least one finger includes a pair of fingers, each of said fingers being received in a respective one of said side channels.

28. A method for securing an implant to the spinal column, comprising:
engaging an anchor member to a vertebra;
positioning an implant in a receiver member, the receiver member extending proximally along a longitudinal axis away from the anchor member;
engaging a securing member to the receiver member; threadingly advancing the securing member into the receiver member distally along the longitudinal axis to contact the implant with an implant engaging surface of the securing member;
rotationally constraining the implant engaging surface as the securing member is threadingly advanced in the receiver member with at least one finger extending distally along the longitudinal axis and beside the implant into a channel of a seat member, wherein the channel opens proximally in the seat member and outwardly of the seat member so that a portion of the seat member is positioned between a distal end of the at least one finger in the channel and the implant in the receiver member: and
engaging the implant between the implant engaging surface and an implant support surface of the seat member in the receiver member.

29. The method of claim 28, wherein engaging the implant fixes the anchor member in a position relative to the receiver member.

30. The method of claim 28, wherein rotationally constraining the implant engaging surface includes positioning at least two fingers extending distally from the securing member into opposite side channels extending along the seat member.

31. The method of claim 30, wherein the securing member includes a receiver engaging portion threadingly engageable with the receiver member and an implant engaging portion engaged distally to and rotatable relative to the receiver engaging portion, said at least one finger extending from the implant engaging portion.

32. The method of claim 28, wherein positioning the implant includes positioning a spinal rod along the spinal column.

33. A method for securing a spinal rod to an anchor member, comprising:
providing a coupling assembly sized for engagement with a vertebra of an animal subject, wherein the coupling assembly includes:
a spinal rod and an anchor member engageable to the vertebra, a receiver member extending from the anchor member in a proximal direction along a longitudinal axis, the receiver member defining a passage for receiving the spinal rod with the passage extending transversely to the longitudinal axis and opening at opposite sides of the receiver member and the spinal rod extending through the opposite sides, the coupling assembly further including a seat member in the receiver member between the spinal rod and the anchor member, the seat member including an implant support surface along the passage that extends between the opposite sides of the passage, and the coupling assembly further includes a securing member including an implant engaging surface that extends between the opposite sides of the passage;
configuring the coupling assembly for engaging the spinal rod in the passage between the implant support surface and the implant engaging surface with the securing member and seat member each extending around the spinal rod in the direction of the longitudinal axis to engage one another in the receiver member; and
limiting engagement stresses exerted on the spinal rod by providing each of the implant engaging surface and the implant support surface in a configuration that conformingly contacts the spinal rod between the opposite sides of the passage to distribute engagement forces, wherein the securing member is configured to engage the coupling assembly so that the implant engaging surface is rotationally constrained as the securing member is threadingly advanced in the receiver member and the implant support surface is formed by a seat member in the receiver member, and rotationally constraining the implant engaging surface includes positioning a distal end of at least one finger extending distally from the securing member into a side channel that is formed in the seat member so that a portion of the seat member is positioned between the distal end of the at least one finger in the channel and the spinal rod.

34. The method of claim 33, wherein the securing member is engageable to a securing position in the receiver member while the implant engaging surface is maintained in aligned relation with the implant support surface.

35. The method of claim 34, wherein said passage defines a length along which the spinal rod extends when positioned therein, wherein when in the securing position the spinal rod is engaged along the length by each of the implant support surface and the implant engaging surface.

* * * * *

UNITED STATES PATENT AND TRADEMARK OFFICE
CERTIFICATE OF CORRECTION

PATENT NO.       : 7,625,394 B2                                                Page 1 of 1
APPLICATION NO.  : 11/197799
DATED            : December 1, 2009
INVENTOR(S)      : Molz, IV et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this

Twenty-sixth Day of October, 2010

David J. Kappos
*Director of the United States Patent and Trademark Office*